US009131887B2

(12) United States Patent
Sato et al.

(10) Patent No.: US 9,131,887 B2
(45) Date of Patent: Sep. 15, 2015

(54) SYSTEM FOR MEASURING MOOD STATE

(71) Applicant: Hitachi, Ltd., Chiyoda-ku, Tokyo (JP)

(72) Inventors: Hiroki Sato, Shiki (JP); Masashi Kiguchi, Kawagoe (JP)

(73) Assignee: Hitachi, Ltd., Tokyo (JP)

( * ) Notice: Subject to any disclaimer, the term of this patent is extended or adjusted under 35 U.S.C. 154(b) by 26 days.

(21) Appl. No.: 13/739,022

(22) Filed: Jan. 11, 2013

(65) Prior Publication Data

US 2013/0253329 A1 Sep. 26, 2013

(30) Foreign Application Priority Data

Jan. 20, 2012 (JP) ................................. 2012-009557

(51) Int. Cl.
*A61B 5/00* (2006.01)
*A61B 5/16* (2006.01)
*A61B 5/1455* (2006.01)

(52) U.S. Cl.
CPC ............. *A61B 5/165* (2013.01); *A61B 5/14553* (2013.01)

(58) Field of Classification Search
CPC ...... A61B 5/165; A61B 5/16; A61N 1/36082; A61N 1/36096; G06F 19/3437
USPC ................................................. 600/407–480
See application file for complete search history.

(56) References Cited

U.S. PATENT DOCUMENTS

| | | | |
|---|---|---|---|
| 7,974,697 B2 * | 7/2011 | Maschino et al. | 607/45 |
| 8,320,649 B2 * | 11/2012 | Shahaf et al. | 382/128 |
| 8,470,548 B2 * | 6/2013 | Svenningsson et al. | 435/7.92 |
| 8,679,009 B2 * | 3/2014 | Osorio | 600/300 |
| 2006/0004422 A1 * | 1/2006 | De Ridder | 607/45 |
| 2007/0173902 A1 * | 7/2007 | Maschino et al. | 607/45 |
| 2008/0241839 A1 * | 10/2008 | Potkin et al. | 435/6 |
| 2009/0297000 A1 * | 12/2009 | Shahaf et al. | 382/128 |
| 2010/0174586 A1 * | 7/2010 | Berg et al. | 705/10 |
| 2011/0306845 A1 * | 12/2011 | Osorio | 600/300 |
| 2011/0306846 A1 * | 12/2011 | Osorio | 600/301 |
| 2012/0289788 A1 * | 11/2012 | Jain et al. | 600/301 |
| 2012/0289789 A1 * | 11/2012 | Jain et al. | 600/301 |
| 2012/0289790 A1 * | 11/2012 | Jain et al. | 600/301 |

(Continued)

FOREIGN PATENT DOCUMENTS

JP 2009-285000 A 12/2009

OTHER PUBLICATIONS

Alan Baddeley, "Working Memory", Science, New Series, Jan. 31, 1992, pp. 556-559, vol. 255, No. 5044.

(Continued)

*Primary Examiner* — Sanjay Cattungal
(74) *Attorney, Agent, or Firm* — Crowell & Moring LLP

(57) ABSTRACT

Disclosed is an system for measuring mood states, which calculate and views high-accurate mood indices from brain activation signals obtained by a non-invasive biospectrometric technology, taking account into differences among individuals, for example cognitive capacity using methods supporting the measurement of mood states of individuals. The system of the present invention stores a plurality of different mood index calculation formulae, selects one of the plurality of mood index calculation formulae based on a personal trait, for example the working memory task performance or working memory capacity of a subject, and substitutes the brain activation data of the subject for the selected calculation formula to calculate and view mood indices.

6 Claims, 10 Drawing Sheets

(56) References Cited

U.S. PATENT DOCUMENTS

| | | | | |
|---|---|---|---|---|
| 2012/0289791 A1* | 11/2012 | Jain et al. | | 600/301 |
| 2012/0289792 A1* | 11/2012 | Jain et al. | | 600/301 |
| 2012/0289793 A1* | 11/2012 | Jain et al. | | 600/301 |
| 2012/0289794 A1* | 11/2012 | Jain et al. | | 600/301 |
| 2012/0290215 A1* | 11/2012 | Adler et al. | | 702/19 |
| 2013/0080127 A1* | 3/2013 | Shahaf et al. | | 703/2 |

OTHER PUBLICATIONS

Todd S. Braver et al., "A Parametric Study of Prefrontal Cortex Involvement in Human Working Memory", Neuroimage, 1997, pp. 49-62, vol. 5, No. N1960247.

Irene E. Nagel et al., "Performance Level Modulates Adult Age Differences in Brain Activation During Spatial Working Memory", PNAS Early Edition, 2009, USA (Six (6) pages).

* cited by examiner

P < 0.05 (CORRECTED)

SPATIAL WM

VERBAL WM (SPATIAL WM −
VERBAL WM)

METHOD ACCORDING TO THE PRIOR ART (CALCULATION FORMULAE TO BE FIXED)

PROVIDED METHOD (CALCULATION FORMULAE TO BE SELECTED)

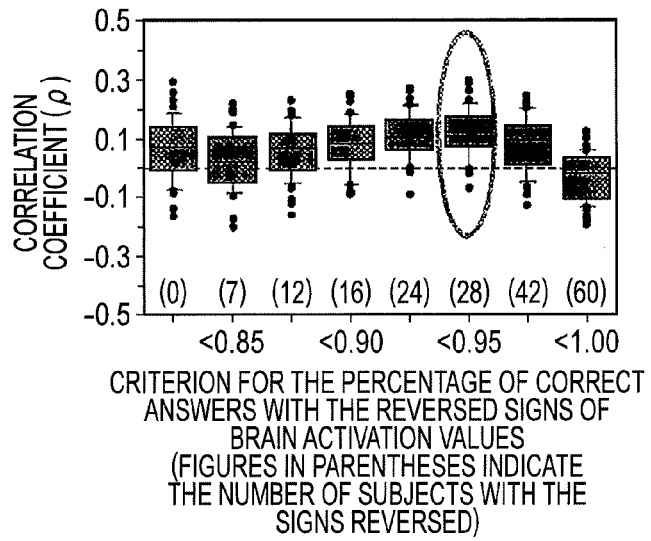
FIG. 10A SPATIAL WM
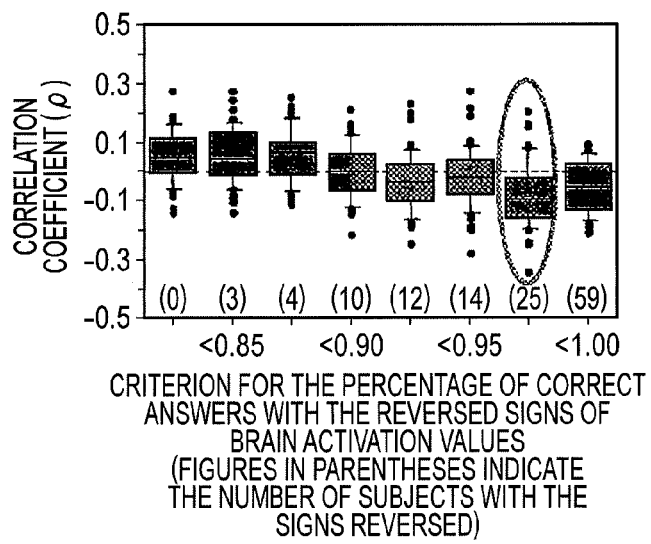
FIG. 10B VERBAL WM
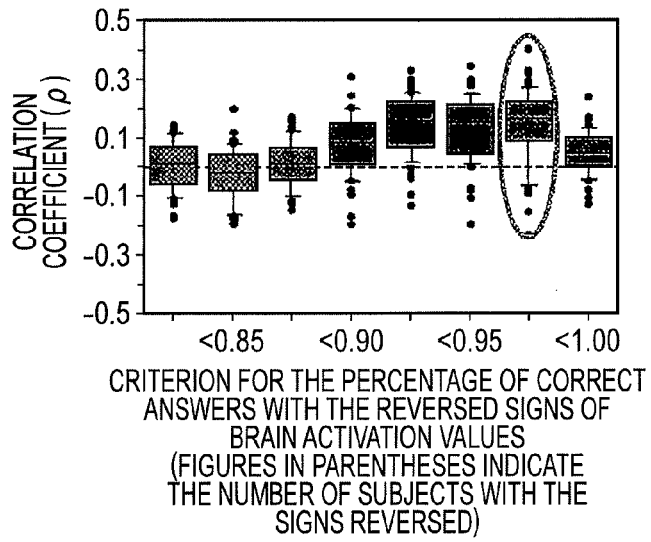
FIG. 10C (SPATIAL WM − VERBAL WM)

SYSTEM FOR MEASURING MOOD STATE

CLAIM OF PRIORITY

The present invention claims priority from Japanese patent application JP 2012-009557 filed on Jan. 20, 2012, the content of which is hereby incorporated by reference into this application.

FIELD OF THE INVENTION

The present invention relates to methods for measuring brain function using near-infrared spectroscopy and more particularly to methods of measuring mood states, which provide mood indices showing subjects' mood states based on differences among individuals in brain activation data.

BACKGROUND OF THE INVENTION

In modern society, the risk for developing mental health problems have increased year after year and mental health maintenance and promotion is an extremely important challenge to be attacked. The objective evaluation of mood states, which is a factor essential to mental health maintenance and promotion, is considered to be effective in detecting a mental disorder at its early stage and measuring the process of recovery from the disorder. The mood states have been measured subjectively based on the results of interviews and questionnaires in many cases while recently, more objective methods for measuring mood states using biometry have been suggested.

Giving an example, a method has been proposed for measuring the mental states of individuals, such as mood and emotion, using a biospectrometric technology, which is capable of measuring a change (hereinafter, referred to as a Hb signal) in relative concentrations among "oxygenated hemoglobin (Hb)", "deoxygenated Hb", and "total Hb (the sum of oxygenated Hb and deoxygenated Hb)" in cerebral cortex by means of any of lights in the visual-to-near-infrared range with high biopermeability (Japanese Unexamined Patent Application Publication No. 2009-285000). Japanese Unexamined Patent Application Publication No. 2009-285000 discloses a method for measuring frontal lobe activation associated with a working memory task using a biospectrometric technology and calculating "mood indices" indicating the mood states of subjects from the obtained values for frontal lobe activation. Working memory (hereinafter, abbreviated to WM in some cases) is the concept of a system, which temporarily stores and manipulates information necessary for various cognitive activities, such as conversation, sentence comprehension, mental calculations, judgment, and inference, and have been advocated as a model for understanding human cognitive function (Baddeley, A., "Working Memory", Science 255, 556-559 (1992)). The working memory task is a cognitive task, which requires working memory (WM). Initially advocated as a cognitive processing model, WM has been recognized as prefrontal cortex function based on the findings of animal tests and clinical data of human patients with brain injury since the late 1980. Recently, moreover, the development of brain function imaging technology has encouraged the investigations of the neural mechanism of prefrontal cortex function. Giving an example, the studies using functional magnetic resonance imaging (fMRI) demonstrated that when a spatial WM task is performed, dorsolateral prefrontal cortex (DLPFC) of a subject works centering on middle frontal gyrus (Braver, T. S., Cohen, J. D., Nystrom, L. E., Jonides, J., Smith, E. E., Noll, D. C., "A parametric study of prefrontal cortex involvement in human working memory", NeuroImage 5, 49-62 (1997)).

The method disclosed in Japanese Unexamined Patent Application Publication No. 2009-285000 is characterized in that such a phenomenon is used that frontal lobe activation induced by a verbal WM task using a phonological loop is negatively correlated with the seriousness of depressed mood of a subject, while a frontal lobe activation signal induced by a non-verbal WM task without the need for the phonological loop tends to be not correlated or positively correlated with the seriousness of depressed mood. This biospectrometric technology is expected to be applied to mood measurement in the daily environment because of its negligible restriction on subjects and easiness to measure.

On the other hand, not only mood states but also various differences among individuals, such as the sexuality, age, and WM capacity, of a subject may affect frontal lobe activation associated with a WM task. Giving an example, Nagel I E, Preuschhof C, Li S C, Nyberg L, Baeckman L, Lindenberger U, Heekeren H R. Performance level modulates adult age differences in brain activation during spatial working memory. Proc Natl Acad Sci USA. 2009; 106(52):22552-7 describes that a brain activation signal associated with a WM task is modified by both of the factors: subject's age and task performance.

SUMMARY OF THE INVENTION

In the biospectrometric technology for measuring frontal lobe activation associated with a working memory (WM) task to evaluate mood states of subjects, a variation in WM capacity or cognitive task performance may affect the accuracy of mood indices. To address this problem, such methods of measuring mood states is sought that take account into the correlation between differences among individuals in WM capacity and mood state. An object of the present invention is to provide methods of calculating higher-accurate mood indices based on differences among individuals in WM capacity.

The system for measuring mood states of the present invention executes the steps of: storing a plurality of calculation formulae for calculating mood indices; selecting an appropriate calculation formula based on personal trait information including the WM capacity and task performance of a subject; and calculating and viewing the mood indices from brain activation data. Namely, a system for measuring mood states according to one typical aspect of the present invention, which is composed of: an input unit for entering measured data of brain activation of a subject associated with a WM task and personal trait information on the WM capacity of the subject; a memory unit for storing a plurality of calculation formulae for calculating mood indices; a calculation unit for calculating mood indices; and an output unit for outputting the calculated mood indices, selects one of the plurality of calculation formulae for calculating mood indices based on the personal trait information, substitutes the brain activation data for the selected calculation formula to calculate mood indices, and outputs the calculated mood indices from the output unit.

The system for measuring mood states of the present invention allows higher-accurate mood indices in a group of subjects, whose mood states could not been accurately measured by methods according to the prior art, to be calculated.

BRIEF DESCRIPTION OF THE DRAWINGS

FIGS. 10A to 10C are box plots showing the distribution of correlation coefficients between brain activation values and depressed mood scores based on a criterion for selecting a calculation formula, FIG. 10A showing a distribution of the correlation coefficients which is derived from measurement results with the spatial WM task, FIG. 10B showing a distribution of the correlation coefficients which is derived from measurement results with the verbal WM task, and FIG. 10C showing a distribution of the correlation coefficients which is derived from measurement results with both of the spatial WM task and the verbal WM task by using selection of one of formula (1) and formula (2).

DETAILED DESCRIPTION OF THE PREFERRED EMBODIMENTS

Figure 1:
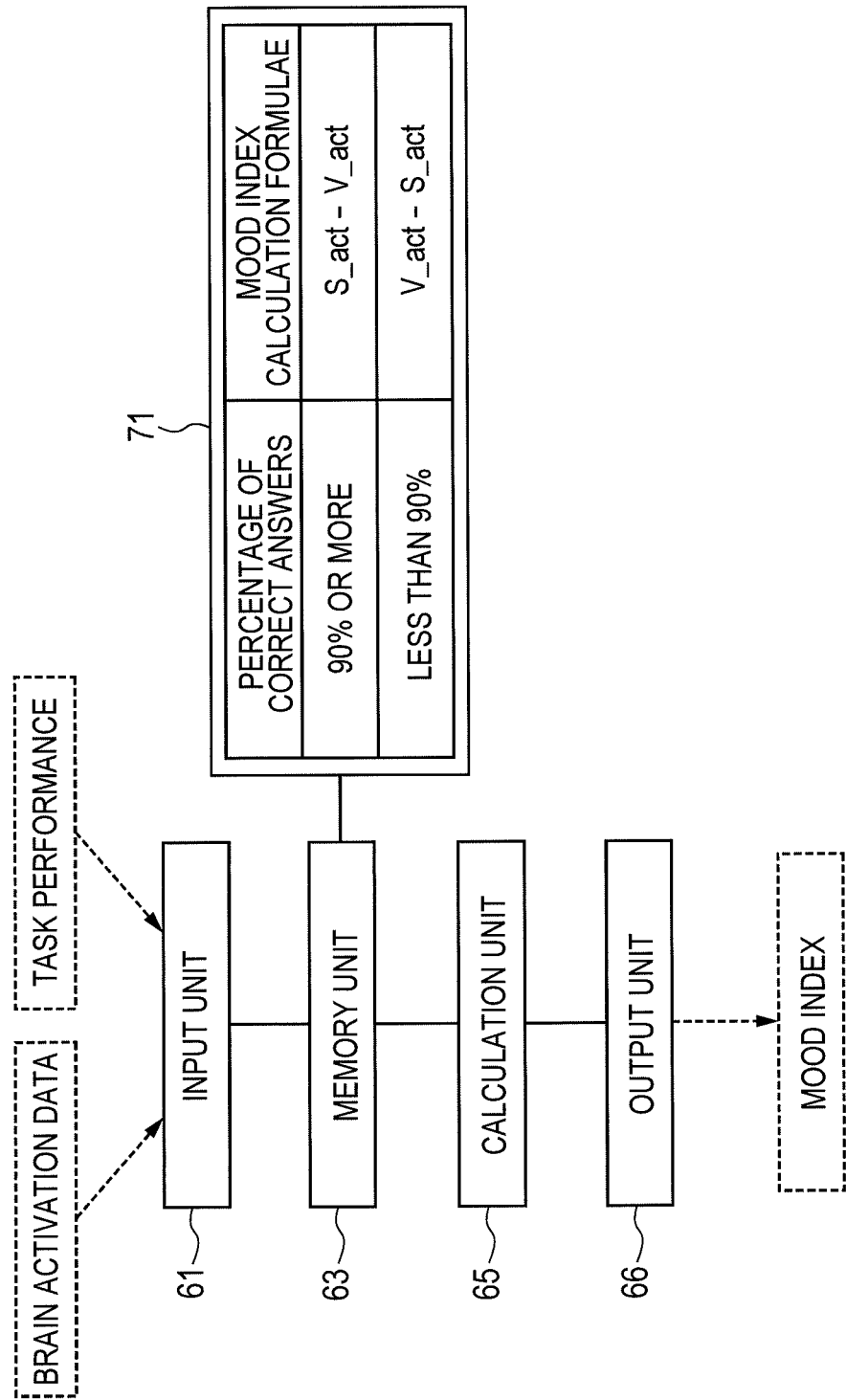
FIG. 1 is a schematic block diagram of a system for measuring mood states according to one aspect of the present invention.

FIG. 1 is a schematic block diagram of a system for measuring mood states according to one aspect of the present invention. The system for measuring mood states of the present invention is composed of: an input unit 61 for entering the brain activation data and task performance of a subject; a memory unit 63 for storing a correspondence table 101 between a plurality of mood index calculation formulae for calculating mood indices, of which typical one is a depressive level (seriousness of depressed mood), of the subject from the measured brain activation data and task performance; a calculation unit 64 for calculating mood indices; and an output unit 67 for outputting the calculated mood indices. The system for measuring mood states of the present invention is, in particular, characterized in that different index calculation formulae corresponding to each of WM task performance classes are stored in the correspondence table 101, one of the stored mood index calculation formulae is selected based on the value for task performance obtained by giving a WM task to a subject, and the brain activation data of the subject is substituted for the selected mood index calculation formula to calculate the mood indices. The significance and effectiveness of the selection of the mood index calculation formula corresponding to the task performance of the subject will be in detail described in reference to accompanying drawings.

Figure 2:
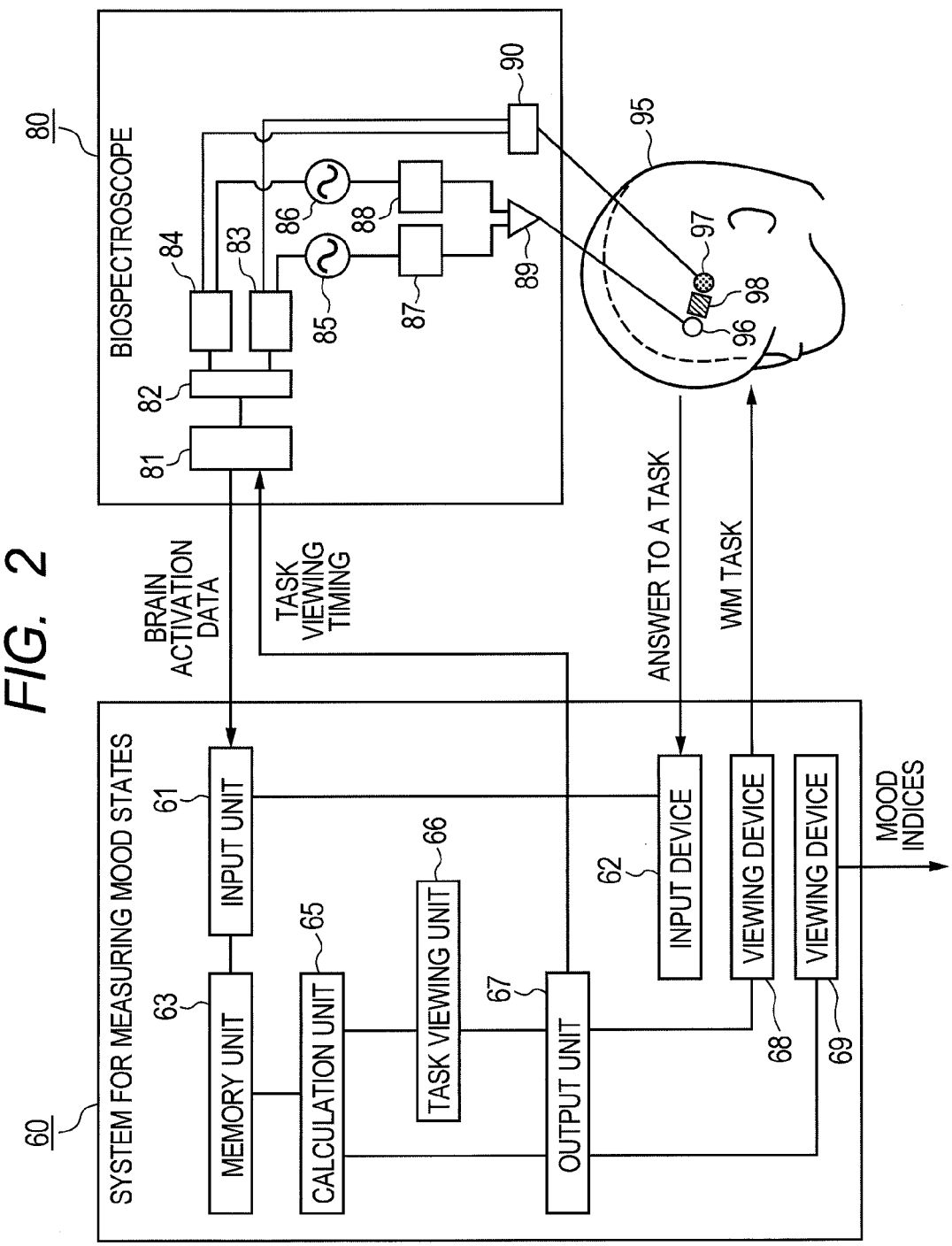
FIG. 2 is a block diagram of the whole composition of the system, which views a working memory (WM) task, measures brain activation data, and calculate mood indices, according to the one aspect of the present invention.

FIG. 2 is a block diagram of the whole composition of the system, which views a working memory (WM) task, measures brain activation data, and calculate mood indices, including a biospectroscope working together with the system for measuring mood states, according to the one aspect of the present invention. The biospectroscope 80 is composed of; two laser diodes 87, 88 with different peak wavelengths; two oscillators 85, 86 for generating signals for modulating the two laser diodes at different frequencies; an optical mixer 89 for mixing two different lights with different peak wavelengths; a light irradiation unit for irradiating the light emitted from the optical mixer 89 in a light-irradiation position 96 of a subject's head 95 via an optical fiber; a light-detector 90 for detecting a mixed light in a light-detection position 97 (according to the one aspect of the present invention, point about 3 cm apart from) moderately apart from the light irradiation unit; lock-in amplifiers 83, 84, to which signals with different modulation frequencies are input from the oscillators 85, 86 as reference signals; an analog-digital converter 82 for converting transmission signals of individual lights with different wavelengths, namely outputs from the lock-in amplifiers 83, 84, from analog to digital signals; and a control PC 81 for controlling measurement timing and processing measured data. An approximate middle point between the light-irradiation position 96 and the light-detection position 97 is the measurement position 98. It should be noted that a head gear equipped with a light-irradiation unit and a light-detector disposed alongside is worn on the subject's head 95 so as to attach to the region of brain function associated with a WM task. Although FIG. 2 shows only one measurement position 98, the use of the oscillators 85, 86 for providing different modulation frequencies, enables a plurality of optical signals to be separated from a light detected in the same detection position. Moreover, the use of a biospectroscope with a plurality of light-irradiation positions 96 and light-detection positions 97 set actually allows measurement at a plurality of measurement positions. Measurement is successfully performed at at least one point of frontal lobe, while it is preferable to provide a plurality of measurement positions to obtain further detailed information. The system according to the aspect of the present invention uses the oscillators to separate a plurality of optical signals; however, it is possible to separate the optical signals by means of pulse light in timing with lighting without oscillators. Alternatively, any of other types of light sources, such as a LED, maybe used and not limited to a laser diode. Transmission signals of lights within each wavelength band are analog-digital converted at the analog-digital converter 82 and then input to the control PC 81. The transmission signals of the light are processed at the control PC 81, sent to the input unit 61 of the system for measuring mood states 60 as brain activation signals, and then stored in the memory unit 63.

The system for measuring mood states 60 shown in FIG. 2 is the same as the system for measuring mood states shown in FIG. 1 and the symbols for blocks shown in FIG. 1 are also used to indicate the same blocks in FIG. 2. It should be noted that the following blocks omitted from FIG. 1 are contained in FIG. 2. A task viewing unit 66 views a task to a subject via an output unit 67 and a viewing device 68, of which typical ones are a display or speaker. A task viewing timing signal is sent to the control PC 81 of the biospectroscope from the output unit 67 for recording. The subject's answer to the task is sent to the memory unit 63 via the input device 62, of which typical ones are a keyboard, gamepad, button, microphone, and camera, from input unit 61. In this way, the brain activation data and the subject's answer data associated with task viewing are recorded in the memory unit 63. A mood index calculation program detailed later is activated and calculates mood indices using these stored data in the calculation unit 65. The calculated mood indices are viewed on the viewing device 69 via the output unit 67. Herein, the viewing device 68 for viewing the task and the viewing device 69 for viewing the mood indices are individually incorporated; however, it is possible to configure the system suitable for subject's self-checking by making one device to serve as these two devices.

The calculated mood indices are stored together with a personal ID and measured information such as measurement date in the memory unit 63. The subject's data stored in the memory unit 63 maybe analyzed to determine what position the subject's data is placed in accumulated population data or how the subject's mood indices have been varied with time and view the results.

Figure 3:
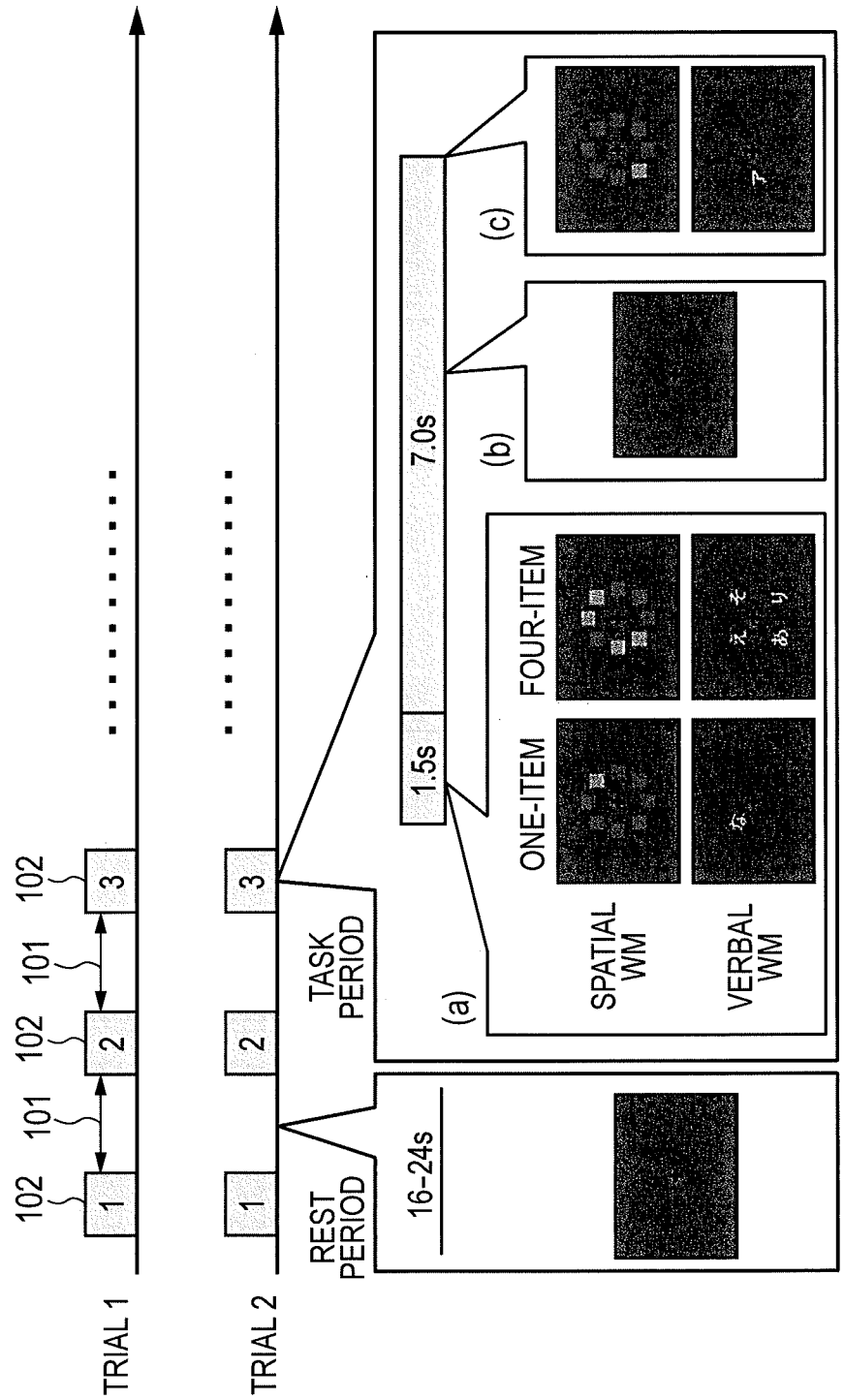
FIG. 3 is a sequence diagram showing the sequence of viewing a working memory (WM) task according to the one aspect of the present invention.

In this aspect of the present invention, a delayed matching paradigm is used as a typical WM task (cognitive task requiring working memory (WM)). The delayed matching paradigm is a task such that a subject is asked to memorize certain information and after a given delay time, it is tested whether the subject has kept memory of the information. In this aspect of the present invention, two WM tasks, one being a spatial WM task to ask the subject to memorize spatial positional information of a square and another being a verbal WM task to ask the subject to memorize phonological information of a word, have been used. In each of these tasks, a one-item condition for memorizing one piece of information and a 4-item condition for memorizing four items have been set. A WM task sequence is shown in FIG. 3. The tasks were performed on each of subjects twice (trial 1, trial 2). For each trial, a total of 16 task periods 102 are set. During each of the task periods 102, the task is followed by a period 101 for keeping rest (rest period 101) by fixing the subject's eyes on a fixation point ("+") viewed on a screen. The length of each rest period 101 is 16 to 24 seconds. During each task period 102, the aforementioned four experimental conditions were repeated in a random order four times. In one task, first, information (target stimulus) to be memorized is viewed for 1.5 seconds (FIG. 3A). Next, after a 7-sec. delay time (FIG. 3B), during which the subject fixes his/her eyes on the cross (+) mark, a probe stimulus used to determine whether his/her memory has been kept is viewed (FIG. 3C). The subject is asked to answer Yes when information on the probe stimulus matches some of the target stimulus and No when it does not match as soon as possible.

Figure 4:
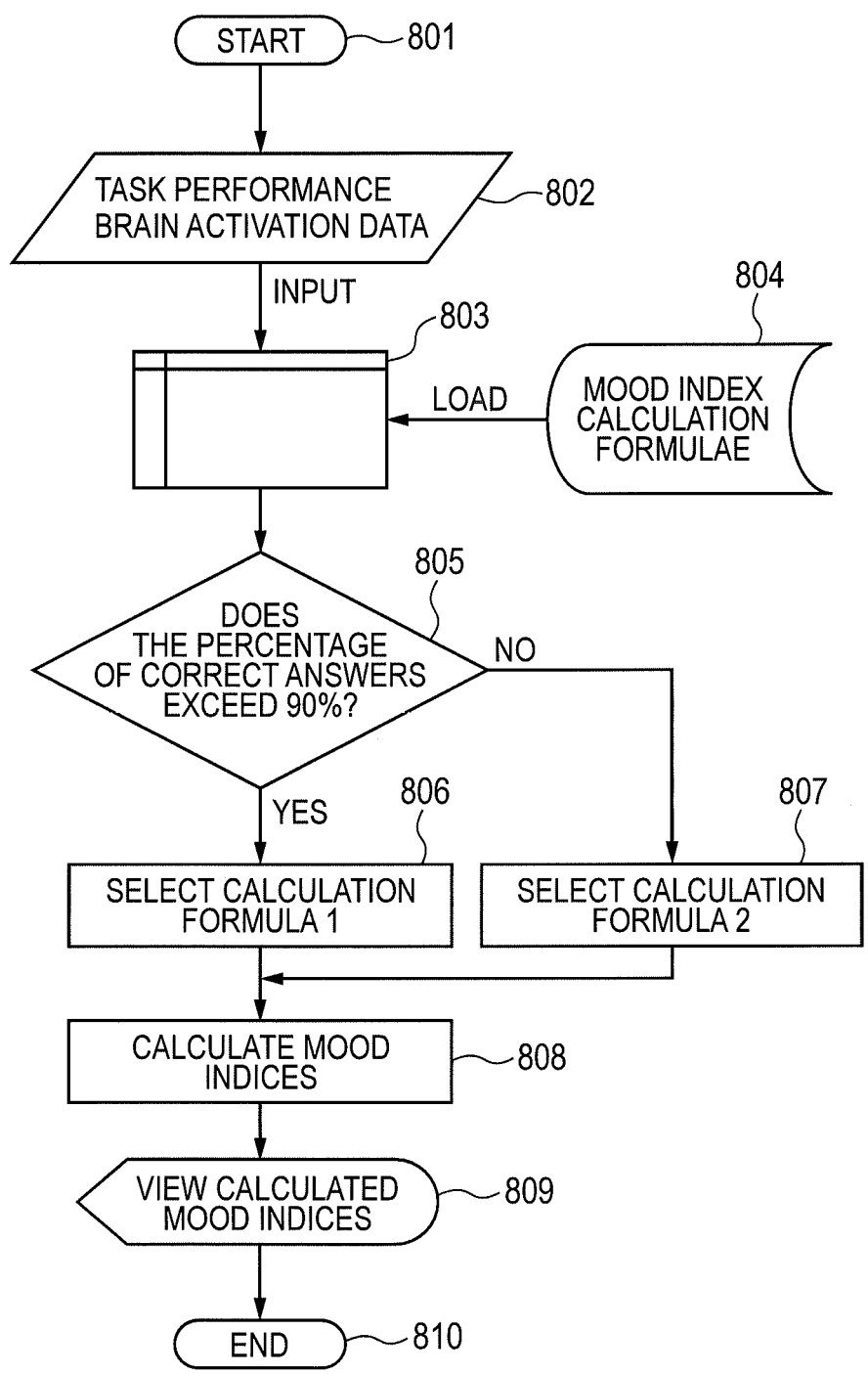
FIG. 4 is a flowchart illustrating the flow of a procedure for calculating the mood indices according to the one aspect of the present invention.

FIG. 4 shows the mood index calculation program executed by the system for measuring mood states 60. This program assumes the previously measured brain activation data and task performance to be input data, while data maybe entered in real time concurrently with brain activation measurement for execution. In this aspect of the present invention, a flow of processing one measured data for one subject is described, but it is possible that data for a plurality of subjects or a plurality of data are repeatedly processed until the mood indices are calculated (in a step 808) and the integrated result is viewed in a step 809.

First, task performance data and brain activation data are entered in main memory (in a step of 803). The task performance data serves as a parameter for selecting a mood index calculation formula. Herein, the task performance data is the answer data to the WM task performed for measuring brain activation data, which includes basically a correct answer count (percentage of correct answers) and reaction time. As for this program, brain activation data on the answer to the task may be directly entered in some cases or previously processed data may be entered in other cases. In this aspect of the present invention, the task performance data obtained from the measurement of the brain activation data is used as the parameter for selecting the mood index calculation formula; however, the parameter is not limited to the task performance data because the present invention focuses on differences arising from personal WM capacity (capability) in correlation between the brain activation data and the depressed mood scores. Giving an example, the value or class for the WM capacity of the subject, which has been evaluated by a preliminary test, may be entered as a parameter. Alternatively, the raw brain activation data measured by biospectroscope may be directly entered or a pre-processed Hb signal may be entered or the value for a brain activation signal calculated by statistic analysis may be entered. In addition to the aforementioned data, the mood index calculation formula stored in a memory unit 804 is read in and an appropriate mood index calculation formula is selected based on the result of the next decision step 805 (in a step 806). Herein, the following (formula 1) is selected with the percentage of correct answers ≥90%, while the following (formula 2) is selected with the percentage of correct answers <90% (806, 807).

$$\text{Mood index} = \frac{\bar{x}_A - \bar{x}_B}{\sqrt{\frac{1}{(n_A + n_B - 2)}(SD_A^2 \cdot n_A + SD_B^2 \cdot n_B)}} \quad \text{(Formula 1)}$$

where,
$\bar{x}_A$: Average signal intensity for task A (spatial WM task),
$\bar{x}_B$: Average signal intensity for task B (verbal WM task),
$n_A$: Number of repetitions for task A,
$n_B$: Number of repetitions for task B,
$SD_A$: Standard deviation for task A, and
$SD_B$: Standard deviation for task B $$\text{Mood index} = \frac{\bar{x}_B - \bar{x}_A}{\sqrt{\frac{1}{(n_A + n_B - 2)}(SD_A^2 \cdot n_A + SD_B^2 \cdot n_B)}} \quad \text{(Formula 2)}$$

The selected mood index calculation formula is used to calculate the mood indices (808) for viewing on a screen, e.g., a PC screen (809). The mood indices may be indicated by means of voice or printed out and not limited to a display screen. On the display screen, they may be viewed not only in terms of numerical values but also using various viewing elements including colors, shapes, and positions.

Thus, in this aspect of the present invention, the calculation formulae is selected for calculating mood evaluation indices from the brain activation data obtained from the subject's answer to the WM task based on the value for percentage of correct answers of the subject to the WM task. The effectiveness of this method and the percentage of correct answers used to select the calculation formula will be described in detail based on the result of an actual empirical experiment.

Figure 5A:
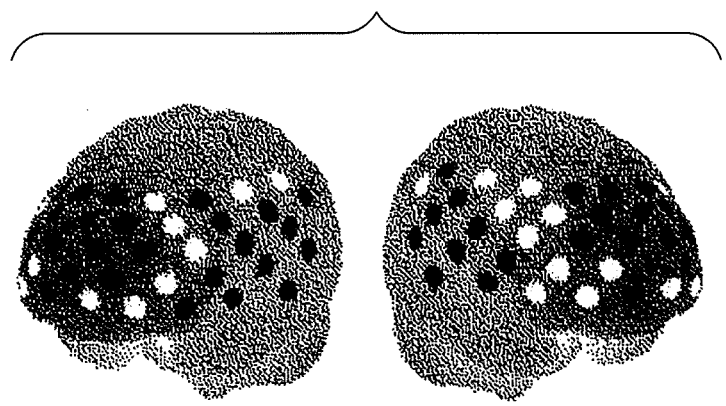
FIG. 5A is a view of brain denoting a result of ANOVA, in which difficulty level of WM task is selected as the contributing factor for variance.
Figure 5B:
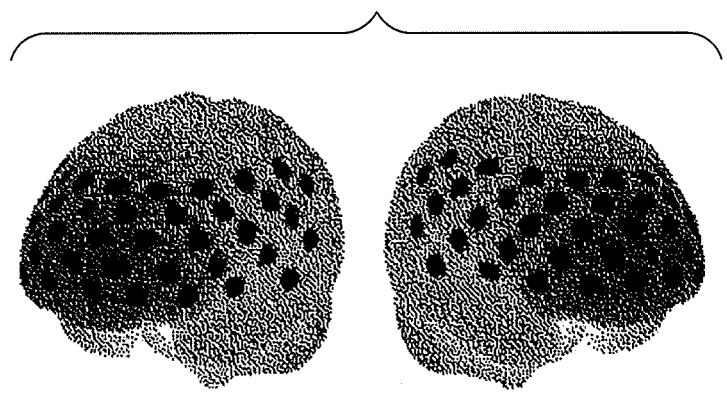
FIG. 5B is a view of brain denoting another result of ANOVA, in which WM condition is selected as the contributing factor for variance.

Brain activation associated with a WM task (cognitive task requiring working memory (WM)) was measured on 90 subjects using a biospectroscope. The subjects included 45 male subject (average age of 33.3 years old) and 45 female subjects (average age of 33.8 years old). A brain activation signal (oxygenated hemoglobin signal) associated with the WM task was measured using the biospectroscope capable of measuring at 52 points on the frontal region of head. The result of a two-way ANOVA performed under the condition of [difficulty (one item, four items)×WM condition (spatial WM, verbal WM)] using an average of the brain activation periods for the individual subjects is shown in FIG. 5. A white circle indicates the measurement position, at which the primary effect of difficulty was significantly observed in FIG. 5A. In the measurement positions, where the primary effect of difficulty was significantly observed, brain activation is powerful under the four-item condition compared with that under the one-item condition, suggesting that the WM load is reflected therein. These measurement positions were observed mainly on dorsolateral prefrontal cortex (DLPFC) and our finding agreed with the result of a previous study on brain activation associated with a WM task. On the other hand, the comparison between spatial and verbal WM tasks showed no significant difference in brain activation in any of 52 measurement positions as shown in FIG. 5B.

Figure 6A:
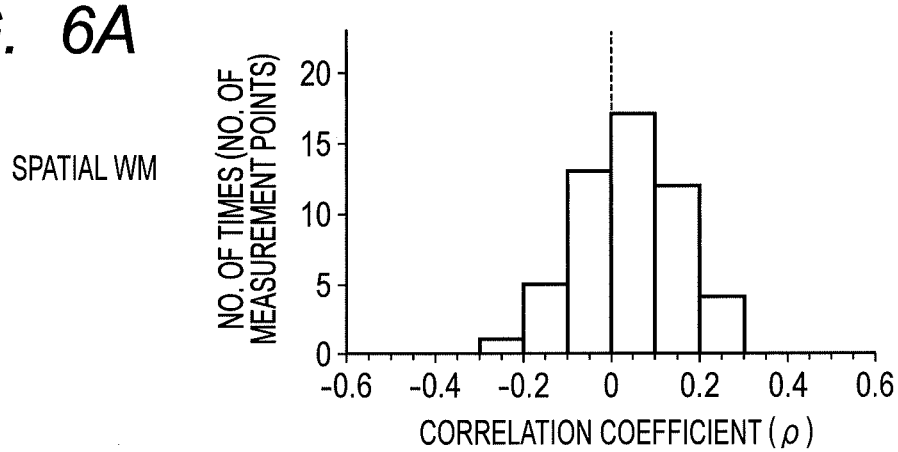
FIGS. 6A to 6C are measurement point histograms of correlation coefficients between brain activation values and depressed mood scores (scores indicating the seriousness of depressed moods) in all the subjects, FIG. 6A being a histogram of the correlation coefficents in case where a spatial WM task is set to the subjects, FIG. 6B being a histogram of the correlation coefficients in case where a verbal WM task is set to the subjects, and FIG. 6C being a histogram of the correlation coefficients on the basis of the differences between brain activation values associated with the spatial WM task and brain activation values associated with the verbal WM task.
Figure 6B:
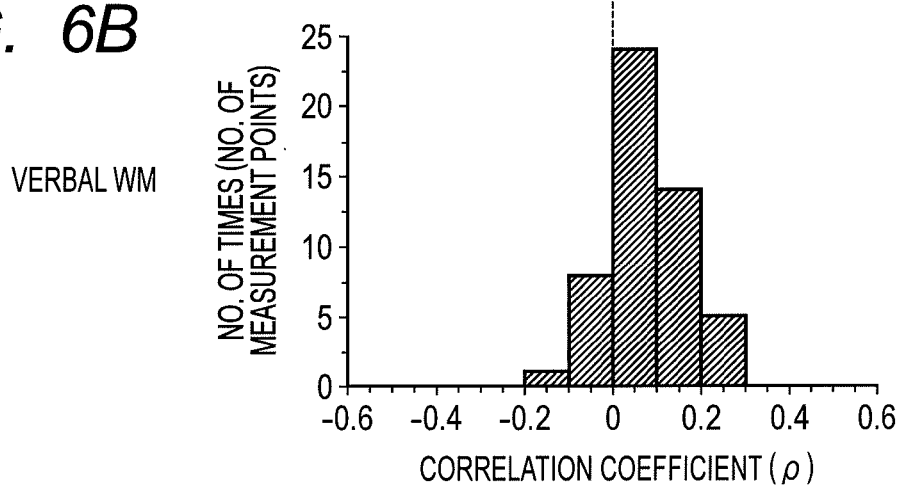
Figure 6C:
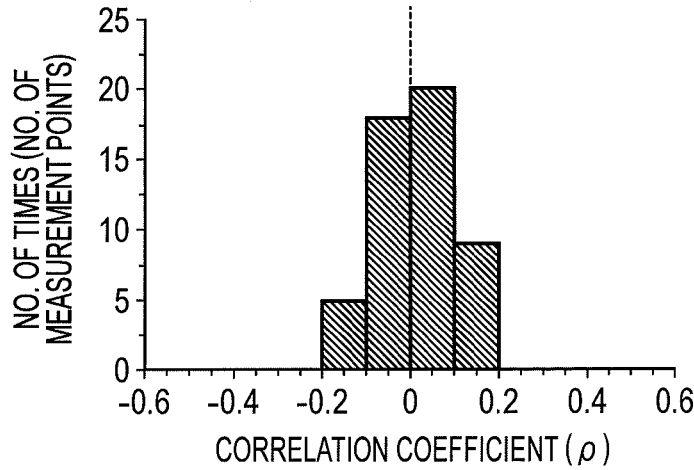

According to Japanese Unexamined Patent Application Publication No. 2009-285000, these brain activation signals are related with the mood states (seriousness of depressed mood) of the individual subjects. Specifically, the brain activation signal associated with a spatial WM task is positively correlated with the mood states, while the brain activation signal associated with a verbal WM task is negatively correlated with them. The depressed mood scores (scores indicating the seriousness of depressed mood) obtained from the questionnaire evaluation of the depressed mood states of the individual subjects were used to discuss the correlation between the brain activation signals and the mood states. A histogram of the correlation coefficients between the brain activation values and the depressed mood scores calculated in the individual measurement positions is shown in FIG. 6. FIG. 6A shows a histogram of the number of measurement positions vs. the correlation coefficients between the brain activation values and the depressed mood scores associated with a spatial WM task and FIG. 6B shows a histogram of the number of measurement positions vs. the correlation coefficients between the brain activation values and the depressed mood scores associated with a verbal WM task. Contrary on our expectation, when data of all the subjects were used, almost no correlation was observed between the brain activation values and the depressed mood scores independently of the task type, spatial or verbal. For this reason, a histogram of the number of measurement positions vs. the correlation coefficients between the brain activation values and the depressed mood scores was drawn using statistic values indicating the differences between the spatial WM and verbal WM tasks, which is recommended by Japanese Unexamined Patent Application Publication No. 2009-285000. As known from FIG. 6B, no tendency to correlation was also observed between the brain activation values and the depressed mood scores.

Subsequently, assuming that the tendency to correlation between the brain activation values and depressed mood scores was dependent on the level of WM capacity, namely WM capability of the subject or the level of task performance associated with the performed WM task, 90 subjects were assigned to a high performance group or a low performance group to review the correlation. The high performance group of 43 subjects (male 23, female 24) gave correct answers to all the tasks under the one-item condition and its percentage of correct answers was 87.5% or higher even under the four-item condition. The low performance group of 47 subjects (male 23, female 24) made mistakes under the one-item condition and its percentage of correct answers was lower than 87.5% under the four-item condition.

Figure 7A:
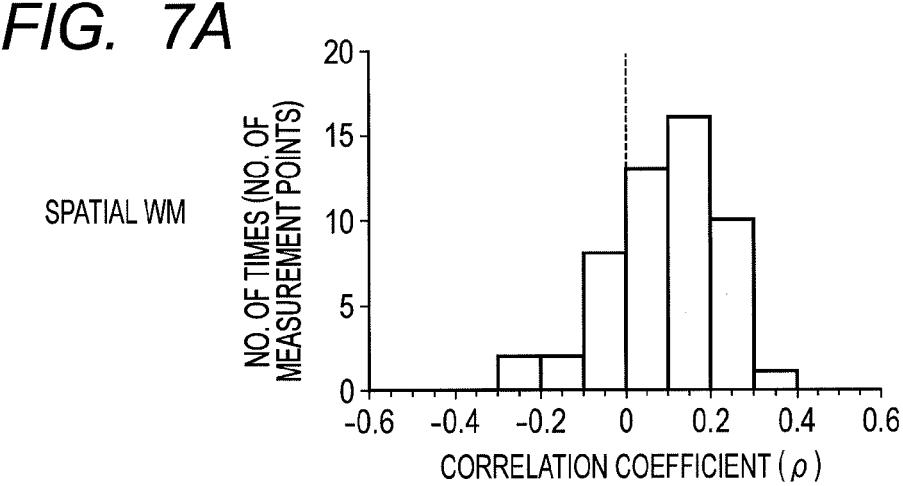
FIGS. 7A to 7C are measurement point histograms of correlation coefficients between brain activation values and depressed mood scores in a high performance group, FIG. 7A being a histogram of the correlation coefficients in the high performance group in case where a spatial WM task is set to the subjects, FIG. 7B being a histogram of the correlation coefficients in the high performance group in case where a verbal WM task is set to the subjects, and FIG. 7C being a histogram of the correlation coefficients on the basis of the differences between brain activation values associated with the spatial WM task and brain activation values associated with the verbal WM task in the high performance group.
Figure 7B:
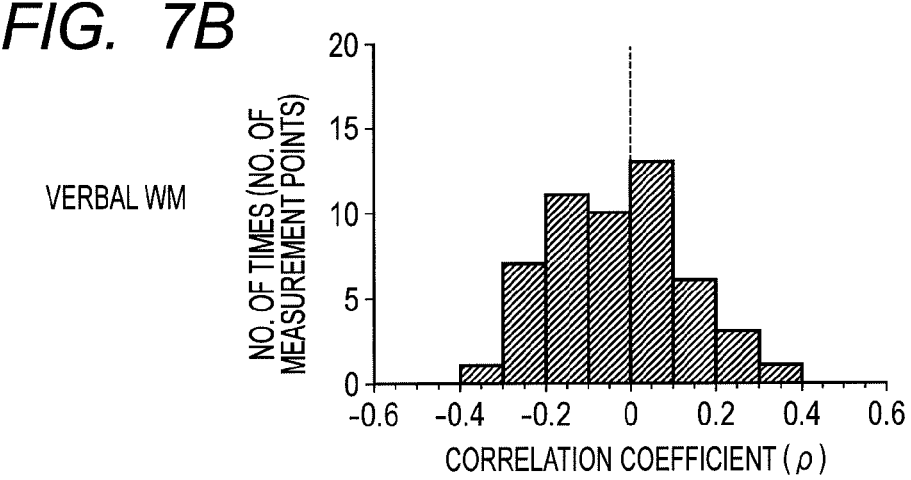
Figure 7C:
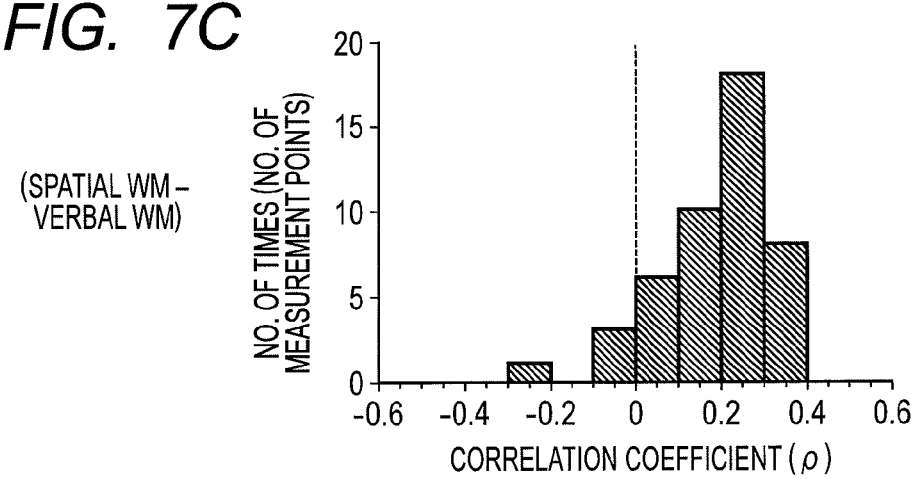

The histogram of the correlation coefficients in the high performance group is shown in FIG. 7. The histogram of correlation coefficients shown in FIG. 7A was obtained from the measurement when the spatial WM task was performed. The histogram of correlation coefficients shown in FIG. 7B was obtained from the measurement when the verbal WM task was performed. The same tendency as that disclosed in Japanese Unexamined Patent Application Publication No. 2009-285000 was verified, suggesting that more measurement positions showed positive correlation associated with the spatial WM task but negative correlation associated with the verbal WM task. For this reason, a histogram of the number of measurement positions vs. the correlation coefficients between the brain activation values and the depressed mood scores was drawn using statistic values indicating the differences in brain activation value between the spatial WM and verbal WM tasks. The histogram is shown in FIG. 7C. The use of the differences (spatial WM—verbal WM) (the differences in brain activation value between both types of WM tasks) revealed the clear tendency to correlation between the brain activation values and depressed mood scores.

Figure 8A:
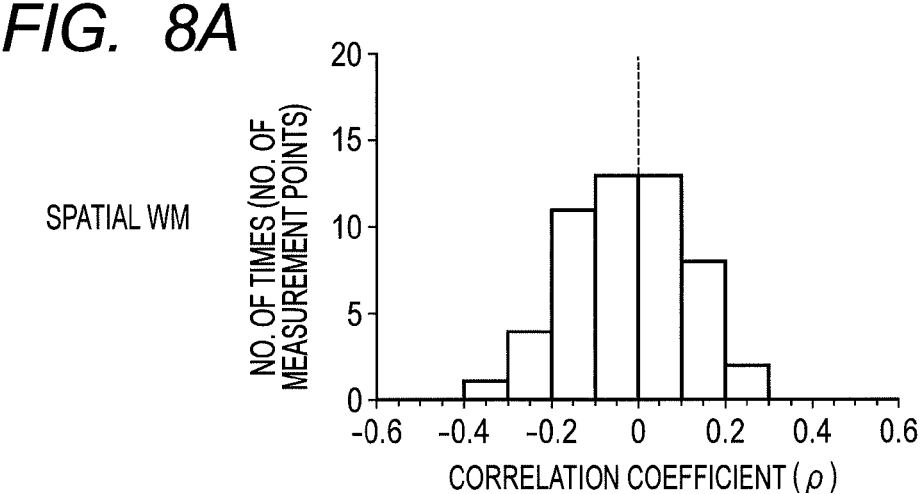
FIGS. 8A to 8C are measurement posit histograms of correlation coefficients between brain activation values and depressed mood scores in a low performance group, FIG. 8A being a histogram of the correlation coefficients in the low performance group in case where a spatial WM task is set to the subjects, FIG. 8B being a histogram of the correlation coefficients in the low performance group in case where a verbal WM task is set to the subjects, and FIG. 8C being a histogram of the correlation coefficients on the basis of the differences between brain activation values associated with the spatial WM task and brain activation values associated with the verbal WM task in the low performance group.
Figure 8B:
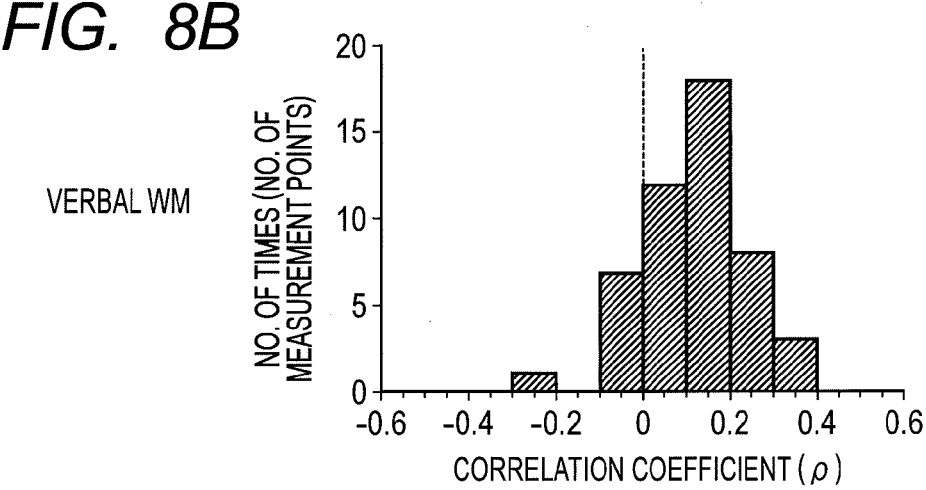
Figure 8C:
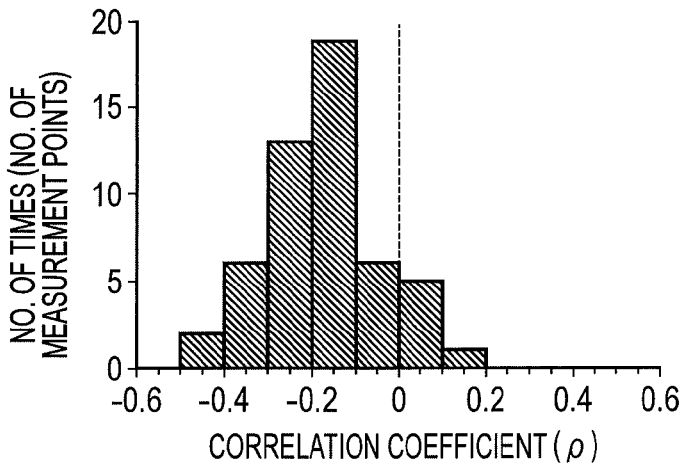

Next, a histogram of correlation coefficients in the low performance group is shown in FIG. 8. As known from FIG. 8, a reverse tendency to that in the high performance group was observed. Specifically, in the histogram (FIG. 8A) of correlation coefficients obtained from the measurement when the spatial WM task was performed, a rather large number of the measurement positions showed negative correlation coefficients, while in the histogram (FIG. 8B) of correlation coefficients obtained from the measurement when the verbal WM task was performed, a large number of measurement positions showed positive correlation coefficients. In other words, a histogram (FIG. 8C), which was drawn using statistic values for the differences in brain activation value between the spatial WM and verbal WM tasks, clarified the result that the measurement positions showed clear negative correlation with depressed mood scores.

Based on the aforementioned experimental results, it is clearly effective that among the calculation formulae for calculating mood indices, a first calculation formula indicating the differences (spatial WM—verbal WM) (differences in brain activation value associated with each of two types of WM tasks) and, a second calculation formula indicating the differences (verbal WM—spatial WM) (differences in brain activation value associated with each of two types of WM tasks) reverse to those of the first calculation formula are prepared in advance, one of the first and second calculation formulae based on the value for percentage of correct answers of the subject to a WM task, and the brain activation data associated with the answer to the WM task is substituted for the selected calculation formula to calculate mood evaluation indices. Without this method, significant mood indices objectively indicating the mood state of the subject may not be calculated.

Figure 9A:
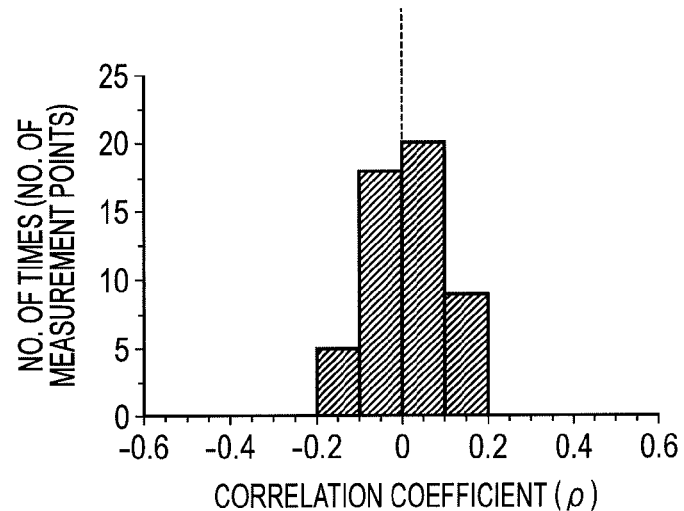
FIG. 9A is a measurement posit histogram of correlation coefficients between brain activation values and depressed mood scores on the basis of the differences between spatial WM task and verbal WM task derived by using a calculation formula fixed regardless of the percentage of correct answers to the WM tasks.
Figure 9B:
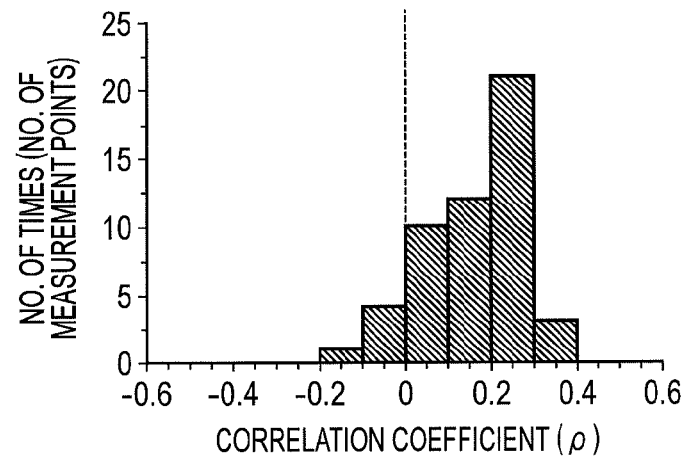
FIG. 9B is a measurement point histogram of the correlation coefficients between brain activation values and depressed mood scores on the basis of the differences between the spatial WM task and the verbal WM task derived by using calculation formulas which are corresponding to the percentage of correct answers to the WM tasks.

FIG. 9 shows the comparison between a histogram (FIG. 9A) of the number of measurement positions vs. the correlation coefficients between the mood indices and the mood scores in all of 90 subjects using a fixed calculation formula regardless of the percentage of correct answers to the WM task, and a histogram (FIG. 9B) of the number of measurements vs. the correlation coefficients between the mood indices calculated using the calculation formulas corresponding to the high performance group and to the low performance group, one of which the subjects were assigned to. As shown in FIG. 9A, when the fixed calculation formula was used, the median of the correlation coefficients on 52 measurement positions was 0.010 and almost no correlation was observed between the calculated mood evaluation indices and the mood scores. In contrast, when the calculation formula was selected based on task performance, the median of the correlation coefficients on 52 measurement positions was 0.198, clearly indicating a positive tendency to correlation as a whole. Thus, as known from the aspect of the present invention, the method, which involves the steps of storing a plurality of different mood index calculation formulae; selecting an appropriate mood index calculation formula based on the task performance of the subject; and calculating and outputting the mood indices of the subject, allows high-accurate mood state measurement.

In a commonly-used method for measuring brain activation, a task is repeated several times under the same condition and the signal components, which response to the task repeatedly, are considered to be activation signals associated with the task. In (formula 1) and (formula 2), the differences in brain activation between task A and task B are represented as statistic values taking account into the reproducibility between repetitions. Definitely, this is only one example of the calculation formula for calculating brain activation signals and not limited to this formula when actually used. Giving an example, the following (formula 3) and (formula 4) also may be used.

$$\text{Mood index} = \frac{\bar{x}_A - \bar{x}_B}{|\bar{x}_A| + |\bar{x}_B|} \quad \text{(Formula 3)}$$

$$\text{Mood index} = \frac{\bar{x}_B - \bar{x}_A}{|\bar{x}_A| + |\bar{x}_B|} \quad \text{(Formula 4)}$$

In the aforementioned aspect of the present invention, an example, in which the subjects were assigned to one of two groups, "high performance group" and "low performance group" based on their task performance or the criterion for classifying WM capacity assuming that the percentage of correct answers equal to 90% in all the subjects was a threshold. In this assumption, a criterion for classifying the subjects in one of two groups, one being composed of the subjects, who give corrects answers to all the tasks under the one-item condition and whose percentage of correct answers is higher than 87.5% under the four-item condition, and another being composed of other subjects simply replaced with the percentage of correct answers equal to 90% as the threshold. In the aforementioned example, it could be verified that the use of either of two criteria for classifying the subjects improved equally the accuracy of mood index calculation. The most suitable criterion for classifying the subjects, however, may vary depending on the difficulty of the task and the characteristic features of the subject groups. To address this problem, the actual data shown in the description of the aforementioned empirical experiment was used to discuss the criterion for classifying the percentages of correct answers, which was capable of increasing the correlation with the depressed mood scores. Specifically, the correlations (a distribution of correlation coefficients on a total of 52 measurement positions) when the sign of the brain activation data of the subject, who showed the percentage of correct answers lower than a given value, was reversed is shown in a box plot (FIG. 10). The upper limit and lower limit of a rectangular indicate 75 percentile and 25 percentile areas of data, respectively; a centerline indicates a 50 percentile (median) area; and an error bar indicates a 90 percentile area. The top 10% of samples and low-ranked 10% of samples were plotted out. Based on the result of the spatial WM task, which showed the positive tendency to correlation with depressed moods by a method independent of the criterion for classifying the subjects based on the percentage of correct answers, a box plot (FIG. 10A) was drawn. As known from the box plot, the correlation coefficients with the depressed mood scores showed most powerful tendency to being positive when the signs of the brain activation values in 28 subjects with percentage of correct answers lower than 95% were reversed. Next, based on the result of the verbal WM task, which showed the negative tendency to correlation with the depressed mood scores by a method independent of the criterion for classifying the subjects based on the percentage of correct answers, a box plot (FIG. 10B) was drawn. As known from the box plot, the correlation coefficients with the depressed mood scores showed most powerful tendency to being negative when the signs of the brain activation values in 28 subjects with percentage of correct answers lower than 95% were reversed. Based on the result of selecting (formula 1) or (formula 2) using both the spatial WM task and the verbal WM task, a box plot (FIG. 10C) was drawn. As known from the box plot, the correlation coefficients tended to be most powerful when (formula 2) was selected for the subjects with percentage of correct answers lower than 97.5%. Even with the threshold of 95% or 97.5%, relatively high correlation was observed; accordingly, it was suggested that a threshold ranging from about 94% to 98% was suitable for the selection of a mood index calculation formula based on the percentage of correct answers.

At least one brain activation data obtained in the measurement position is sufficient to evaluate the correlation coefficient with the depressed mood scores. On the other hand, when brain activation data are obtained in a plurality of measurement positions, it is possible that the measurement position, at which the most powerful tendency to correlation is shown, is selected or an average or median of the values obtained in a plurality of measurement positions is used. Three or more criteria for classifying the subjects may be used rather than two criteria.

What is claimed is:

1. A system for measuring mood states comprising:
a measuring apparatus configured to repeatedly measure a signal of a first brain activation value during a reaction in a brain of a subject to a first type of cognitive task requiring spatial working memory and a signal of a second brain activation value during a reaction in the brain of the subject to a second type of cognitive task requiring verbal working memory;
an input unit for entering measured data of the first and second brain activation values and personal trait information on working memory capacity of the subject;
a memory unit for storing a plurality of calculation formulae for calculating mood indices on the basis of a difference between the first brain activation value and the second brain activation value;
a calculation unit for calculating mood indices; and
an output unit for outputting the calculated mood indices,
wherein the calculation unit selects one of the plurality of calculation formulae for calculating mood indices based on the personal trait information; substitutes the first and second brain activation values into the selected calculation formula to calculate mood indices; and outputs the calculated mood indices from the output unit.

2. The system for measuring mood states according to claim 1, wherein a percentage of correct answers or a reaction time to a cognitive task performed for measuring the first and second brain activation values is used as the personal trait information on the working memory capacity of the subject.

3. The system for measuring mood states according to claim 1, wherein a result of quantitative evaluation of the working memory capacity of the subject is used as the personal trait information on the working memory capacity of the subject.

4. The system for measuring mood states according to claim 1, wherein the first and second brain activation values are obtained from a measurement using a biospectroscope equipped with a light source for irradiating a light onto the head of the subject and a detector for detecting the light transmitted through the head of the subject.

5. The system for measuring mood states according to claim 1, wherein the brain activation data is a signal of frontal lobe obtained from the forehead of the subject.

6. The system for measuring mood states according to claim 1, wherein the first and second brain activation values are brain activation signals measured during either a first working memory task or a second working memory task, and the mood index calculation formulae are those for calculating a relative value using both the brain activation signal, which is measured during the first working memory task, and the brain activation signal, which is measured during the second working memory task.

* * * * *